United States Patent [19]

Huebner et al.

[11] Patent Number: 4,471,127

[45] Date of Patent: Sep. 11, 1984

[54] 1-5-BIS-(1,4-BENZODIOXIN-2-yl)-3-AZA-PENTANE-1,5-DIOLS

[75] Inventors: Charles F. Huebner, Chatham; Heinz W. Gschwend, New Providence, both of N.J.

[73] Assignee: Ciba-Geigy Corporation, Ardsley, N.Y.

[21] Appl. No.: 411,933

[22] Filed: Aug. 26, 1982

Related U.S. Application Data

[60] Division of Ser. No. 299,261, Sep. 8, 1981, Pat. No. 4,380,653, which is a continuation-in-part of Ser. No. 196,503, Oct. 14, 1980, Pat. No. 4,313,955.

[51] Int. Cl.$^3$ .......................................... C07D 319/14
[52] U.S. Cl. .................................................. 549/366
[58] Field of Search ......................................... 549/366

[56] References Cited

U.S. PATENT DOCUMENTS

| | | | |
|---|---|---|---|
| 3,312,592 | 4/1967 | Chodnekar et al. | 549/366 |
| 3,755,413 | 8/1973 | Koppe et al. | 549/437 |
| 4,187,313 | 2/1980 | Gschwend et al. | 549/552 |
| 4,212,808 | 7/1980 | Gschwend et al. | 549/362 |
| 4,261,907 | 4/1981 | Gschwend et al. | 549/551 |

*Primary Examiner*—Ethel G. Love
*Attorney, Agent, or Firm*—Norbert Gruenfeld

[57] ABSTRACT

The novel 1-(2,3-dihydro-1,4-benzodioxin-2S-yl)-5-(2,3-dihydro-1,4-benzodioxin-2R-yl)-3-azapentane-1R,5S-diol, and pharmaceutically acceptable acid addition salts thereof, are efficacious antihypertensive and bradycardic agents. Pharmaceutical compositions, methods of preparation and novel intermediates are described.

3 Claims, No Drawings

1-5-BIS-(1,4-BENZODIOXIN-2-YL)-3-AZAPENTANE-1,5-DIOLS

CROSS-REFERENCE TO RELATED APPLICATION

This is a divisional application of application Ser. No. 299,261 filed Sept. 8, 1981, now U.S. Pat. No. 4,380,653 which is a continuation-in-part of application Ser. No. 196,503 filed Oct. 14, 1980, now U.S. Pat. No. 4,313,955.

BACKGROUND OF THE INVENTION

According to J. Med. Chem. 13, 169 (1970) "Compound 26" of the Formula I, of unspecified stereochemical composition,

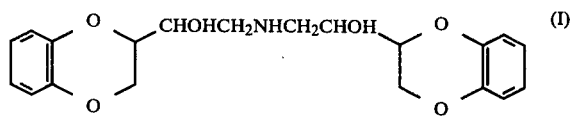

has been obtained as a "by-product in the preparation of 6 and 7", i.e., the erythro and threo "1-(1,4-benzodioxan-2-yl)-2-aminoethanols". According to said publication "compound 26" increases heart rate and inhibits isoproterenol induced tachycardia. Structural Formula I may represent any possible stereoisomers of both the erythro and threo series, i.e., the (SRSR), (RSSR), (SRRS), (RRSS), (RSRR), (SRSS), (RSSS), (SRRR), (RRRR) and (SSSS); the (SRSR) and (RRSS) isomers being the meso-compounds, and the remaining are racemates.

Taking advantage of stereospecific syntheses of intermediates invented by the Applicants' (U.S. Pat. Nos. 4,187,313 and 4,212,808) specific isomers of either the erythro or threo series can now be prepared. Surprisingly it was found that the (SRSR)-meso-compound of Formula II below, belonging to the erythro series, is a superior antihypertensive agent with bradycardic activity.

SUMMARY OF THE DISCLOSURE

The present invention concerns and has for its object the provision of the novel, specific stereoisomer 1-(2,3-dihydro-1,4-benzodioxin-2S-yl)-5-(2,3-dihydro-1,4-benzodioxin-2R-yl)-3-azapentane-1R,5S-diol of Formula II

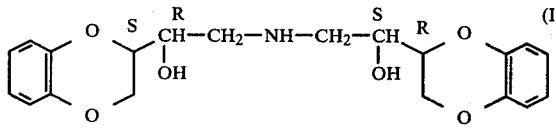

of pharmaceutically acceptable acid addition salts thereof; as well as of corresponding pharmaceutical compositions and of methods for the preparation and application of these products, which are useful antihypertensive and bradycardic agents.

DESCRIPTION OF THE PREFERRED EMBODIMENTS

Said acid addition salts are preferably those prepared with the use of a pharmaceutically acceptable acid or anion exchange preparation, but a resulting salt can also be converted into the corresponding free base of Formula II, for example, with the use of a stronger base, such as a metal or ammonium hydroxide, a basic salt or a cation exchange preparation, e.g., an alkali metal hydroxide or carbonate. Said acid addition salts are, for example, those of pharmaceutically acceptable inorganic or organic acids, such as strong metalloidic acids, preferably hydrohalic, e.g., hydrochloric or hydrobromic acid; sulfuric, phosphoric, nitric or perchloric acid; aliphatic or aromatic carboxylic or sulfonic acids, e.g., formic, acetic, propionic, succinic, glycollic, lactic, malic, tartaric, citric, ascorbic, maleic, hydroxymaleic, pyruvic, phenylacetic, benzoic, 4-aminobenzoic, anthranilic, 4-hydroxybenzoic, salicylic, 4-aminosalicylic, pamoic, nicotinic; methanesulfonic, ethanesulfonic, hydroxyethanesulfonic, ethylenesulfonic, halogenbenzenesulfonic, toluenesulfonic, naphthalenesulfonic, sulfanidic or cyclohexylsulfamic acid. These or other salts, for example, the picrates, can also be used for purification of the base obtained, which is converted into salts, the salts are separated and the base is liberated from the salts. In view of the close relationship between the free compound, and the compound in the form of its salts, whenever any compound is referred to in this context, a corresponding salt is also intended, provided such is possible or appropriate under the circumstances.

The compounds of the invention exhibit valuable pharmacological properties, primarily antihypertensive and moderate bradycardic effects. This is demonstrable by animal tests, using advantageously mammals, e.g., rats or dogs, as test objects, preferably genetically hypertensive rats or renal hypertensive dogs. Said compounds can be applied to them enterally or parenterally, advantageously orally, for example, within gelatin capsules or in the form of starchy suspensions or aqueous solutions, respectively. The applied dosage may range between about 0.01 and 50 mg/kg/day, preferably between about 0.1 and 25 mg/kg/day, advantageously between about 1 and 10 mg/kg/day. The lowering effect on the blood pressure is recorded either directly by means of a catheter, for example, placed in the dog's femoral artery, or indirectly by sphygmomanometry at the rat's tail, and a transducer, expressing the blood pressure prior and after dosing in mm Hg. Thus, for example, the 1-(2,3-dihydro-1,4-benzodioxin-2S-yl)-5-(2,3-dihydro-1,4-benzodioxin-2R-yl)-3-azapentane-1R,5S-diol monomesylate, a representative member of the compounds of this invention, is a very efficacious antihypertensive agent when administered orally to spontaneously hypertensive rats and renal hypertensive dogs. There is no tolerance to its antihypertensive action when given repeatedly, and the blood pressure reduction is accompanied by a slight to moderate reduction in the heart rate. Antihypertensive doses produce neither untoward side-effects in the hypertensive animals, nor in sophisticated animal behavioral models. Said compound is a β-adrenoceptor blocking agent whose potency is less than that of propranolol, which has no antihypertensive activity in the dog and weak activity in the rat hypertensive models. This antihypertensive effect, therefore, appears to be reliant predominantly on mechanisms other than β-adrenoceptor blockade and there is no evidence of a cerebrally located mechanism of action. However, there is evidence suggestive of peripheral vasodilation which makes an important contribution to the impressive antihypertensive efficacy of the compounds of this invention. Accordingly, they are useful antihypertensive and bradycardic agents, for example in the treatment or management of primary, secondary or chronic hypertension. They are also useful intermediates in the preparation of other valuable products, especially of pharmacologically active compositions.

The compounds of the invention are prepared according to methods known per se, advantageously by:

(1) reacting compounds of Formulae III and IV

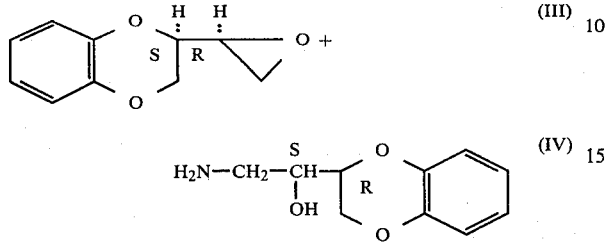

or the respective antipodes thereof, or racemates thereof:

(2) hydrogenolyzing or hydrolyzing a compound of Formula V or an isomeric mixture containing a compound of formula V

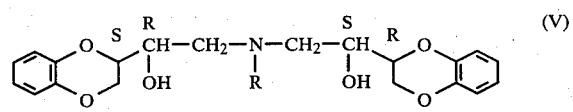

wherein R is an α-aralkyl e.g. benzyl, benzhydryl, trityl or an acyl radical e.g. lower alkanoyl, unsubstituted or substituted benzoyl; or hydrolyzing compounds of formula V wherein R is acyl and one of the hydroxy groups is protected with an acyl radical; or (3) heating compound of formula III or racemate thereof with ammonia, preferably one half molar equivalent; and, if necessary separating the resulting mixture of isomers and, if desired, converting any resulting compound into another compound of the invention.

The starting material of Formulae III and IV is preferably prepared according to our process which comprises the following steps:

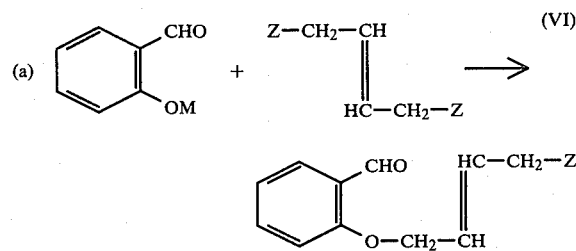

wherein M is one equivalent of a metal atom and Z a halogen atom;

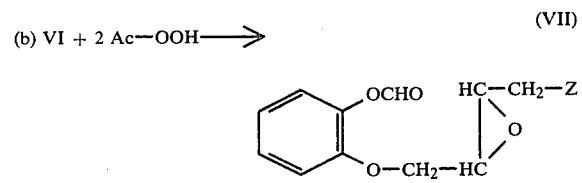

wherein the radical Ac is lower alkanoyl, haloalkanoyl, unsubstituted or substituted benzoyl or phthaloyl; and (c) ring-closing said oxirans of the Formula VII with a hydroxy ion donating agent, to yield after separation of isomers via diasteroisomeric derivatives the compound of Formula III and its antipode, which may be converted to the carbinolamine of Formula IV by means of reactions known to the art and exemplified herein.

Variously, said compound of Formula III may be prepared by condensing the following compounds:

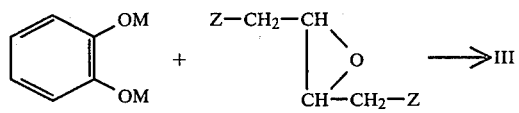

wherein M and Z have the above-given meaning, advantageously in the presence of diluents, such as lower alkylformamides or -sulfoxides and between about 50° and about 70°.

The d,l-erythro-compounds IV obtained from d,l-erythro III and comprising the R,S- and S,R-enantiomers, can be separated with the use of optically active acids, such as mandelic or tartaric acid, camphorsulphonic acid or by derivatization with 1-(1-naphthyl)ethyl isocyanate. Such separation is advantageously carried out as described for the compounds V below, or according to J. Org. Chem. 43, 3803 (1978). Said starting material III may also be prepared by the chiral synthesis exemplified herein, utilizing an asymmetric isocyanate for the preparation of a chromatographically separable mixture.

In the starting material of Formula V, the amino protecting group R is preferably said mono- to tricyclic araliphatic radical, such as benzyl, α-phenethyl, benzhydryl or trityl, unsubstituted in the benzene rings, or substituted therein by lower alkyl, e.g., methyl or ethyl; lower alkoxy, e.g., methoxy or ethoxy; hydroxy; halogeno, e.g., chloro or bromo; or nitro. Said acyl radical R is preferably lower alkanoyl, e.g., formyl, acetyl or propionyl; lower alkoxycarbonyl or carbobenzoxy; carbamoyl; sulfamoyl; aliphatic or aromatic sulfonyl, e.g., mesyl or tosyl; or aroyl, e.g., benzoyl or benzoyl substituted by lower alkyl, lower alkoxy or halogen as defined above.

Depending on the neutral or acidic character of said protecting groups R, they are split off either by hydrogenolysis, for example, with catalytically activated or nascent hydrogen, e.g., hydrogen in the presence of palladium, or generated electrolytically, as in the former instances; whereas said acyl compounds V are advantageously cleaved with the use of aqueous acids or bases, or such salts, for example hydrochloric, trifluoroacetic or methanesulfonic acid; or aqueous alkali metal hydroxides or carbonates, e.g., sodium or potassium hydroxide or carbonate. In case of said sulfur-containing acyl groups, also reducing agents may be used, such as complex light metal hydrides, e.g., lithium aluminum hydride.

The starting material of Formula V, e.g, wherein R is benzyl, is easily obtained by recrystallization of the erythro mixture of diastereomers obtained from said oxiran of Formula III, and its antipode (i.e., racemic erythro oxiran) with the amine R-NH₂, preferably of salts thereof, for example, the hydrochloride or maleate, which come out of solution easily, leaving the undesired stereoisomers in solution. Said recrystallization is preferably carried out in anhydrous or aqueous lower alkanols, such as ethanol, n- or i-propanol. This separation is another aspect of our invention, because stereoisomeric mixtures of compounds with R=H are difficult to separate via crystallization, even in the simple case of three isomers present (i.e., SRSR, RSSR and SRRS); the latter mixture of isomers may be separated chromatographically. The starting material of formula V, e.g. wherein R is acyl, may be obtained as follows:

(a) reacting the aminoalcohol of formula IV, its racemate or antipode, with an acyl halide or equivalent wherein acyl preferably represents lower alkanoyl, benzoyl or benzoyl substituted by lower alkyl, lower alkoxy or halogen;

(b) treating the resulting erythro 2-(2-acylamino-1-hydroxyethyl)-2,3-dihydro-1,4-benzodioxin with a dehydrating agent, e.g. thionyl chloride in pyridine;

(c) reacting the resulting erythro 2-(2-aryl or lower alkyl-4,5-dihydrooxazol-5-yl)-2,3-dihydro-1,4-benzodioxin, wherein aryl preferably represents phenyl or phenyl substituted by lower alkyl, lower alkoxy or halogen, with the oxiran of formula III, its racemate or antipode.

The above-mentioned reactions are carried out according to standard methods, in the presence or absence of diluents, preferably such as are inert to the reagents and are solvents thereof, of catalysts, condensing agents and/or inert atmospheres, at low temperatures, room temperature or elevated temperatures, at atmospheric or superatmospheric pressure.

The invention further includes any variant of the disclosed process, in which an intermediate product obtainable at any stage thereof is used as a starting material and any remaining steps are carried out or the process is discontinued at any stage thereof, or in which a starting material is formed under the reaction conditions, or in which the reaction components are used in the form of their salts or optically pure antipodes.

The pharmacologically active compounds of the invention are useful in the manufacture of pharmaceutical compositions comprising an effective amount thereof in conjunction or admixture with excipients suitable for either enteral or parenteral administration. Preferred are tablets and gelatin capsules comprising the active ingredient together with (a) diluents, e.g., lactose, dextrose, sucrose, mannitol, sorbitol, cellulose and/or glycine, (b) lubricants, e.g., silica, talcum, stearic acid, its magnesium or calcium salt and/or polyethyleneglycol, for tablets also (c) binders, e.g., magnesium aluminum silicate, starch paste, gelatin, tragacanth, methylcellulose, sodium carboxymethylcellulose and/or polyvinylpyrrolidone, if desired, (d) disintegrants, e.g., starches, agar, alginic acid or its sodium salt, or effervescent mixtures and/or (e) absorbents, colorants, flavors and sweeteners. Injectable compositions are preferably aqueous isotonic solutions or suspensions, and suppositories are advantageously prepared from fatty emulsions or suspensions. Said compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Said compositions are prepared according to conventional mixing, granulating or coating methods, respectively, and contain about 0.1 to 90%, preferably about 1 to 75%, of the active ingredient. A unit dosage for a mammal of about 50 to 70 kg weight may contain between about 10 and 100 mg of the active ingredient.

The following examples are intended to illustrate the invention and are not to be construed as being limitations thereon. Temperatures are given in degrees Centigrade, and all parts wherever given are parts by weight. If not mentioned otherwise, all evaporations are performed under reduced pressure, preferably between about 15 and 100 mmHg.

EXAMPLE 1

The mixture of 150 g of 3-benzyl-1-(2,3-dihydro-1,4-benzodioxin-2S-yl)-5-(2,3-dihydro-1,4-benzodioxin-2R-yl)-3-azapentane-1R,5S-diol, 995 ml of glacial acetic acid and 7.5 g of 10% palladium on carbon is hydrogenated at 40° and 3.4 atm until the hydrogen uptake ceases. The mixture is filtered, the filtrate poured into 2,000 ml of water, the mixture cooled to 10° and basified with 1,500 ml of 28% aqueous ammonia. The precipitate formed is filtered off, washed four times with 500 ml of water and dried at 40° and 6 mmHg, to yield the 1-(2,3-dihydro-1,4-benzodioxin-2S-yl)-5(2,3-dihydro-1,4-benzodioxin-2R-yl)-3-azapentane-1R,5S-diol melting at 139°–141°.

The suspension of 180 g thereof in 1,230 ml of anhydrous ethanol is heated to 78° under nitrogen, when dissolution occurs. The solution is stirred and slowly cooled to room temperature overnight, the resulting crystals collected, washed twice with 35 ml of ethanol and dried at 50° and 6 mmHg, to yield said compound in crystalline form, melting at 143°–145°.

To the solution of 148.6 g thereof in 1,500 ml of anhydrous ethanol 43 g of 98% methanesulfonic acid are added at 65° and the solution stirred for three minutes at said temperature. The mixture is stirred and cooled to 20° during one hour, filtered, the residue washed three times with 80 ml of ethanol and dried at 90° and 0.5 mmHg, to yield the monomesylate of said compound melting at 215°–217° with decomposition.

The starting material is prepared according to the new process disclosed as follows:

To 130 lt of ethanol, 12.1 kg of sodium methoxide are added while cooling and stirring, followed by 26.5 kg of salicylaldehyde at 30°. Thereupon 33.3 kg of trans-1,4-dichloro-2-butene are added and the mixture heated to 68° for 4 hours. It is combined with 156 lt of toluene, 187 lt of water and 9.4 kg of 36% hydrochloric acid while keeping the temperature at about 30°. The precipitate formed is filtered off and washed with 16 lt of toluene. The filtrate is separated, the organic layer washed 3 times with 27 lt of water, evaporated, the residue distilled and the fraction boiling at 170°/0.2 mmHg collected, to yield the 2-(4-chloro-trans-2-butenyloxy)-benzaldehyde.

23.0 kg thereof are added to the solution of 63.4 kg of m-chloro-perbenzoic acid in 342 lt of methylene chloride, held at 30°–35°, during 90 minutes. The mixture is refluxed for 48 hours, cooled to room temperature and combined with a sufficient amount of 17% aqueous sodium bisulfite, until the potassium iodide/starch test is negative. The mixture is filtered, the residue washed with 20 lt of methylene chloride, the filtrate separated and the organic layer, containing the 2-(4-chloro-trans-2,3-epoxy-butyloxy)-phenol formate, collected.

It is diluted with 50 lt of methylene chloride and 125 lt of methanol, and combined with 16.6 kg of 85% technical grade potassium hydroxide in 130 lt of water at 20°–25°. The mixture is stirred for 16 hours at said temperature, the organic layer separated and washed with 50 lt of water multiple times, until the pH of 6.0–7.5 is reached. It is evaporated below 40°/20–50 mmHg, and 93 kg of the crude residue are dissolved in 33 lt of isopropanol at 60°–70°. The solution is cooled to 25°–28°, seeded, gradually cooled to −8° and allowed to stand overnight at said temperature. The precipitate formed is filtered off, washed with 22 lt of isopropanol at −10°, and dried at room temperature and reduced pressure, to yield the d,l-erythro-2-oxiranyl-1,4-benzodioxan melting at 50°–53°; it is the racemate consisting of the compound of Formula III and its RS antipode.

Variously, said intermediate may also be obtained according to the other process mentioned previously, thus: to the solution of 7,250 g of m-chloroperbenzoic acid in 4,500 ml chloroform is added 4,125 g of trans-1,4-dichloro-2-butene during 15 minutes while stirring under nitrogen at room temperature. After one hour the mixture is refluxed for 48 hours and stirred at 10° for 1 hour. It is filtered, the residue washed twice with 4,000 ml of chloroform, and the combined filtrates are washed three times with 5,000 ml of 0.5N aqueous sodium hydroxide and water each. They are dried, evaporated, the residue distilled and the fraction boiling at 87°–89°/20 mmHg collected, to yield the trans-2,3-bischloromethyloxiran.

To the solution of 1,390 g thereof and 1,095 g of catechol in 9,870 ml of dimethylsulfoxide, 711 g of sodium hydroxide pellets are added while stirring under nitrogen at 8°. Stirring is continued overnight at room temperature, whereupon 49,000 ml of water are quickly added. The mixture is extracted four times with 10,000 ml of diethyl ether, the extract washed with 8,000 ml of water, dried and evaporated. The residual oil is distilled and the fraction boiling at 76°–102°/0.05 mmHg collected, to yield the d,l-erythro-2-oxiranyl-1,4-benzodioxan, i.e., the 2,3-dihydro-2-(2S-oxiranyl)-1,4-2R-benzodioxan (and its RS antipode) melting at 46°–48°.

2,886 g thereof are added all at once to the solution of 777 g of benzylamine in 16,200 ml of isopropanol while stirring, at room temperature under nitrogen. The mixture is stirred at 98° for five hours, cooled to 30° and combined with 678 ml of concentrated hydrochloric acid. Stirring is continued overnight at room temperature and the resulting suspension diluted with 4,000 ml of isopropanol. It is filtered, the residue washed four times with 2,000 ml of isopropanol and dried at 50° and 6 mmHg, to yield a crude mixture of three stereoisomers.

2,936 g thereof are dissolved in 44,000 ml of methanol at 65° and the solution stirred under nitrogen while slowly cooling to room temperature overnight. The precipitate formed is collected, washed twice with 1,000 ml of methanol and recrystallized twice more, to yield the 3-benzyl-1-(2,3-dihydro-1,4-benzodioxin-2S-yl)-5-(2,3-dihydro-1,4-benzodioxin-2R-yl)-3-azapentane-1R,5S-diol hydrochloride melting at 215°–217°.

To the suspension of 2,602 g thereof in 28,000 ml of water, 4,000 ml of saturated aqueous ammonium hydroxide are added while stirring at room temperature under nitrogen. After two hours 46,000 ml of diethyl ether are added, agitation is stopped and the organic layer separated. The aqueous layer is extracted once more with 15,200 ml of diethyl ether, the combined extracts are dried, filtered and evaporated, to yield the corresponding free base melting at 108°–110°.

EXAMPLE 2

The mixture of 5 g of 3-benzyl-1-(2,3-dihydro-1,4-benzodioxin-2S'-yl)-5-(2,3-dihydro-1,4-benzodioxin-2R-yl)-3-azapentane-1R,5S-diol, 50 ml of acetic acid and 0.5 g of 10% palladium-on-carbon is hydrogenated at 3.0 atm and 25° until one molar equivalent of hydrogen has been absorbed. It is filtered, evaporated, the residue basified with aqueous sodium hydroxide and extracted with methylene chloride. The extract is dried, evaporated, the residue taken up in ethanol and the solution acidified with ethanolic hydrogen chloride, to yield the 1-(2,3-dihydro-1,4-benzodioxin-2S-yl)-5-(2,3-dihydro-1,4-benzodioxin-2R-yl)-3-azapentane-1R,5S-diol hydrochloride hemihydrate melting at 150°–152° with decomposition.

Drying of the salt at 100° under high vacuum for 3 days gives the anhydrous hydrochloride salt melting at 165°–166° with decomposition.

The starting material is prepared as follows: The mixture of 9 g of dl-erythro-2-oxiranyl-1,4-benzodioxan and 2.4 g of benzylamine is stirred under nitrogen at 100° for three hours. The cooled mixture is taken up in isopropanol, made acidic with 4N ethanolic hydrogen chloride and after 24 hours the crystalline mixture of the hydrochloric acid salts of the meso and racemic 3-benzyl-1-(2,3-dihydro-1,4-benzodioxin-2-yl)-5-(2,3-dihydro-1,4-benzodioxin-2-yl)-3-azapentane-1,5-diol of the erythro series is filtered off, m.p. 120°–150° (dec).

Said hydrochlorides are suspended in water, the mixture made basic and extracted with methylene chloride. The extract is dried, evaporated and the residue of the corresponding bases chromatographed on alumina, using chloroform, one quarter saturated with concentrated ammonium hydroxide, as eluent, to yield the (SRSR) meso compound at Rf=0.85, and the (RSSR, SRRS) racemate at Rf=0.55.

Alternatively and more practically, 14.6 g of said basic mixture of meso compound and racemate is dissolved in 200 ml of isopropanol and treated with 4.1 g of maleic acid. After standing two weeks at room temperature, the crystalline maleate of the desired meso compound completely separates, and the mother liquor contains said racemic salt, which salts are converted into the free bases as shown in Example 1.

Said racemic (RSSR) and (SRRS) base mixture is catalytically debenzylated, as shown above for the (SRSR) meso base, to yield the corresponding racemic (RSSR, SRRS) hydrochloride hemihydrate melting at 205° with decomposition.

EXAMPLE 3

As mentioned above, Formula I depicts in fact "10 possible stereoisomers", and the configuration of the single (SRSR) isomer of formula II, which has the desired pharmacological properties, is proven according to the following two procedures:

(1) The hot solution of 1.13 g of the above-described (SRSR) base, 0.71 g of d-10-camphorsulfonic acid and 10 ml of isopropanol is allowed to cool to room temperature and 1.4 g of the resulting crystalline camphorsulfonate is recrystallized eight times from isopropanol. The base regenerated from the eighth recrystallized product shows an $[\alpha]_D^{25}=0°$ (2% in DMSO). In the like manner 0.88 g of the (RSSR, SRRS) racemate, mentioned above, and 0.32 g of d-malic acid in 3 ml of hot isopropanol is allowed to cool to room temperature. The crystals obained are recrystallized twice from isopropanol and the base regenerated from this salt shows an $[\alpha]_D^{25}=-7.33°$ (3% in DMF). Thus, the product which could be resolved is hereby shown to be the racemate, and the former compound must be the meso compound.

(2) The mixture of 0.59 g of said (SRSR) base, 0.23 g of 1-1-phenyethylisocyanate and 5 ml of methylene chloride is refluxed overnight under nitrogen and evaporated to yield the corresponding urea. A parallel experiment with said racemic base and the 1-isocyanate gave another urea preparation. The $^{13}$C nuclear magnetic resonance spectra of both preparations were measured on a Bruker 90.52 MHz instrument in CDCl$_3$ with TMS as a standard. The signals for the two aliphatic carbons of the phenethylamine moiety of the meso-derived urea were two single-line signals at 52.587 and 23.179 p.p.m.

The corresponding signals from the racemate-derived urea were two doublet signals at 52.857, 52.776 and 23.152, 23.044 p.p.m., respectively. This is in accord with the expectation that reaction of a meso base with a chiral isocyanate gives but one urea, whereas the reaction of a racemic base with a chiral isocyanate gives two ureas, which are diastereomeric isomers.

EXAMPLE 4

The mixture of 2.0 g of 2R-(1S-hydroxy-2-aminoethyl)-1,4-benzodioxan, 1.8 g of 2S-(1R-oxiranyl)-1,4-benzodioxan and 20 ml of isopropanol is refluxed overnight. After cooling it is acidified with 4N ethanolic hydrogen chloride and the resulting hydrochloride hemihydrate filtered off, m.p. 150°–152°; it is identical with that of Example 2, $[\alpha]_D^{25} = 0°$ (2% in DMSO).

The starting materials are prepared as follows: To the solution of 8 g of thiophenol in 150 ml of tetrahydrofuran, cooled in ice, is added 4 g of 50% sodium hydride in mineral oil while stirring under nitrogen. After the hydrogen-evolution has ceased, 12.8 g of dl-erythro-2-oxiranyl-1,4-benzodioxan are added and the mixture is allowed to warm to room temperature. It is refluxed for two hours, cooled, acidified with 10% hydrochloric acid and evaporated. The residue is taken up in diethyl ether, the solution washed with water and evaporated to yield the dl-erythro-2-(2-phenylthio-1-hydroxyethyl)-1,4-benzodioxan. It is taken up in 50 ml of toluene, the solution combined with 14 g of (R)-N-[1-(1-naphthyl)-ethyl]-isocyanate and 1% N,N-dimethylethanolamine and the mixture refluxed for six hours. It is evaporated and the residue chromatographed on neutral alumina using hexane-methylene chloride (5:1) as eluting agent and monitoring the eluate in the UV-spectrum at 280 mμ. The first fraction is collected and evaporated, to yield the N-[1R-(1-naphthyl)-ethyl]-1S-(1,4-benzodioxan-2R-yl)-2-phenylthioethylcarbamate. The second fraction from the chromatogram is collected and evaporated to yield the N-[1R-(1-naphthyl)-ethyl]-1R-(1,4-benzodioxan-2S-yl)-2-phenylthioethylcarbamate.

To the solution of 18.8 g of said first fraction product in 200 ml of methylene chloride and 10.2 ml of triethylamine is added dropwise the solution of 3.4 ml of trichlorosilane in 50 ml of methylene chloride and the mixture is refluxed overnight. It is cooled, washed with saturated aqueous ammonium chloride and evaporated, to yield the erythro-2R-(2-phenylthio-1S-hydroxyethyl)-1,4-benzodioxan.

To the stirred solution thereof in 60 ml of methylene chloride 4 g of trimethyloxonium fluoroborate are added and stirring is continued until all the salt is dissolved (three hours). Then 47 ml of 10% aqueous sodium hydroxide are added while stirring and after three hours the organic layer is separated, dried and evaporated, to yield 3.4 g of the desired 2R-(1S-oxiranyl)-1,4-benzodioxan of sufficient purity for further reaction. A purified sample can be obtained by distillation of the above material in a Kugelrohr at 130° and 0.1 mmHg. This epoxide melts at 65° and has an $[\alpha]_D^{25} = -48.6°$ (2% in CHCl$_3$).

The second fraction product of said diastereomeric carbamate (obtained from the above-described chromatography) is treated in the analogous manner, to yield the 2S-(1R-oxiranyl)-1,4-benzodioxan which, when purified as described above, has a m.p. 65° and $[\alpha]_D^{25} = +48.8°$.

The mixture of 10 g of 2R-(1S-oxiranyl)-1,4-benzodioxan, 3 g of sodium azide and 50 ml of dimethylformamide is stirred at 90° for 8 hours. Most of the dimethylformamide is distilled off and the residue diluted with water and extracted with cyclohexane. The extract is washed with water, dried, evaporated and the resulting crude azide dissolved in 50 ml of tetrahydrofuran. This solution is added dropwise to the stirred and cooled solution of 3 g of lithium aluminum hydride in 100 ml of tetrahydrofuran. After completed addition the mixture is refluxed for two hours, cooled in ice and decomposed by the successive addition of 3 ml of water, 3 ml of 15% aqueous sodium hydroxide and 9 ml of water. The inorganic salts are filtered off, washed with diethyl ether, the filtrate dried and evaporated, to yield the 2R-(1S-hydroxy-2-aminoethyl)-1,4-benzodioxan as a sufficiently pure oil.

EXAMPLE 5

To the solution of 6 g of 1,3-bisacetyl-1-(2,3-dihydro-1,4-benzodioxin-2S-yl)-5-(2,3-dihydro-1,4-benzodioxin-2R-yl)-3-azapentane-1R,5S-diol in 100 ml of isopropanol, 15 ml of concentrated hydrochloric acid are added, and the mixture refluxed for 48 hours. It is evaporated, the residue triturated with isopropanol, filtered off and recrystallized from ethanol, to yield said hydrochloride hemihydrate of Examples 2 or 4, melting at 150°–152°.

The starting material is prepared as follows:
To the mixture of 3 g of 2R-(1S-hydroxy-2-aminoethyl)-1,4-benzodioxan and 10 ml of pyridine, 3 ml of acetic anhydride are added while stirring at room temperature. After 6 hours it is evaporated, the residue taken up in methylene chloride, the solution washed with 5% hydrochloric acid and 5% aqueous sodium bicarbonate, dried and evaporated.

The residual bisacetyl derivative is dissolved in 15 ml of dimethylformamide, and the solution combined with 0.74 g of 50% sodium hydride in mineral oil while stirring at room temperature. After 2 hours, 2.7 of 2S-(1R-oxiranyl)-1,4-benzodioxan are added, and the mixture stirred for 24 hours at room temperature under nitrogen. It is evaporated and the residue triturated with petroleum ether; this is dissolved in water, neutralized with dilute hydrochloric acid and extracted with methylene chloride to yield the 1,3-bisacetyl-1-(2,3-dihydro-1,4-benzodioxin-2S-yl)-5-(2,3-dihydro-1,4-benzodioxin-2R-yl)-3-azapentane-1R,5S-diol.

EXAMPLE 6

A solution of 5.0 g of d,l-erythro-2-oxiranyl-2,3-dihydro-1,4-benzodioxin in 50 ml methanol and 2.0 ml concentrated ammonium hydroxide is heated in a sealed tube at 100° C. for 3 days. The dark liquid is evaporated in vacuo, dissolved in ethyl acetate and shaken with 30 ml of 1N HCl solution. The precipitated solid is filtered off and air dried to yield 1-(2,3-dihydro-1,4-benzodioxin-2-yl)-5-(2,3-dihydro-1,4-benzodioxin-2-yl)-3-azapentane-1,5-diol hydrochloride consisting of a crude mixture of meso and d,l isomers. This is converted to the free base and purified by reverse phase high pressure liquid chromatography on a cyanopropyl bonded silica gel column with a solvent consisting of 80% methanol and 20% of 0.05% aqueous ammonium carbonate to yield as the fastest moving component the meso isomer namely the 1-(2,3-dihydro-1,4-benzodioxin-2S-yl)-5-(2,3-dihydro-1,4-benzodioxin-2R-yl)-3-azapentane-1R,5S-diol melting at 139°-141°, identical to compound of example 1.

EXAMPLE 7

A solution of 0.45 g of the crude meso and d,l-erythro 3-benzoyl-1-(2,3-dihydro-1,4-benzodioxin-2-yl)-5-(2,3-dihydro-1,4-benzodioxin-2-yl)-3-azapentane-1,5-diol in a solution of 1.0 g of potassium hydroxide in 5 ml of methanol and 0.5 ml of water is heated under reflux overnight.

After dilution with $H_2O$, the oily mixture is extracted several times with 1N HCl. The acidic, aqueous layer is made basic with dilute NaOH solution and extracted with ether to yield a crude oil. The oil is dissolved in isopropanol, and ethanolic HCl is added. The precipitated solid is filtered off to yield 1-(2,3-dihydro-1,4-benzodioxin-2-yl)-5-(2,3-dihydro-1,4-benzodioxin-2-yl)-3-azapentane-1,5-diol hydrochloride consisting of a crude mixture of meso and d,l isomers. This is converted to the free base and purified by reverse phase high pressure liquid chromatography as described in example 6 to yield the meso isomer 1-(2,3-dihydro-1,4-benzodioxin-2S-yl)-5-(2,3-dihydro-1,4-benzodioxin-2R-yl)-3-azapentane-1R,5S-diol identical to compound of example 1.

The starting material is prepared as follows:

A solution of 12.0 g of benzylamine in 20 ml isopropanol is heated to reflux and 10.0 g of d,l-erythro-2-oxiranyl-2,3-dihydro-1,4-benzodioxin in 40 ml isopropanol is added dropwise. The solution is refluxed overnight and evaporated to dryness in vacuo. After the addition of water, the oily mixture is extracted several times with ether. Upon shaking the ether solution with 3N HCl, a solid precipitates out. A recrystallization from isopropanol yields d,l-erythro-2-(2-benzylamino-1-hydroxyethyl)-2,3-dihydro-1,4-benzodioxin hydrochloride melting at 167°-9°.

A mixture of 5.0 g of d,l-erythro-2-(2-benzylamino-1-hydroxyethyl)-2,3-dihydro-1,4-benzodioxin hydrochloride in 190 ml ethanol, 10 ml water and 0.5 g 10% palladium on carbon is hydrogenated at 50 lbs pressure. The catalyst is filtered off and the filtrate is evaporated to dryness in vacuo to give d,l-erythro-2-(2-amino-1-hydroxyethyl)-2,3-dihydro-1,4-benzodioxin hydrochloride, melting at 227°-9°.

2.5 g of d,l-erythro-2-(2-amino-1-hydroxyethyl)-2,3-dihydro-1,4-benzodioxin (free base) is dissolved in 25 ml of pyridine and cooled in an ice bath as 1.8 ml of benzoyl chloride is added dropwise. The solution is stirred at room temperature for 3 days and evaporated to dryness in vacuo to obtain 4.5 g of crude product melting at 95°-115°. Two recrystallizations from ethanol yield d,l-erythro-2-(2-benzamido-1-hydroxyethyl)-2,3-dihydro-1,4-benzodioxin, melting at 145°-8°.

A mixture of 2.5 g of d,l-erythro-2-(2-benzamido-1-hydroxyethyl)-2,3-dihydro-1,4-benzodioxin and 9.2 ml of thionyl chloride is stirred at room temperature for three minutes and then heated on a steam bath for two minutes. After evaporation to dryness, dilute sodium hydroxide is added and the mixture is extracted with ether to yield 1.4 g of crude product. Recrystallization from ethanol gives d,l-erythro-2-(2-phenyl-4,5-dihydrooxazol-5-yl)-2,3-dihydro-1,4-benzodioxin melting at 114°-5°.

d,l-erythro-2-(2-phenyl-4,5-dihydrooxazol-5-yl)-2,3-dihydro-benzodioxin (0.3 g) and d,l-erythro-2-oxiranyl-2,3-dihydro-1,4-benzodioxin (0.19 g) are heated together at 100° overnight. Addition of ether precipitates residual starting material. The filtrate containing erythro 3-benzoyl-1-(2,3-dihydro-1,4-benzo-dioxin-2-yl)-5-(2,3-dihydro-1,4-benzodioxin-2-yl)-3-azapentane-1,5-diol as a mixture of meso and d,l isomers is evaporated to dryness and the crude product is used directly in the above hydrolysis to the desired product.

EXAMPLE 8

Preparation of 10,000 tablets each containing 5 mg of the active ingredient:

Formula 1-(2,3-dihydro-1,4-benzodioxin-2S-yl)-5-(2,3-dihydro-1,4-benzodioxin-2R-yl)-3-azapentane-1R,5S-diol monomesylate: 50.00 g.
Lactose: 1,157.00 g.
Corn Starch: 75.00 g.
Polyethylene glycol 6,000: 75.00 g.
Talcum powder: 75.00 g.
Magnesiun stearate: 18.00 g.
Purified water: q.s.

Procedure

All the powders are passed through a screen with openings of 0.6 mm. Then the drug substance, lactose, talcum, magnesium stearate and half of the starch are mixed in a suitable mixer. The other half of the starch is suspended in 40 ml of water and the suspension added to the boiling solution of the polyethylene glycol in 150 ml of water. The paste formed is added to the powders which are granulated, if necessary, with an additional amount of water. The granulate is dried overnight at 35°, broken on a screen with 1.2 mm openings and compressed into tablets using concave punches with 6.5 mm diameter, uppers bisected.

EXAMPLE 9

Preparation of 10,000 capsules each containing 20 mg of the active ingredient:

Formula 1-(2,3-dihydro-1,4-benzodioxin-2S-yl)-5-(2,3-dihydro-1,4-benzodioxin-2R-yl)-3-azapentane-1R,5S-diol hydrochloride hemihydrate: 200.0 g.
Lactose: 1,800.0 g.
Talcum powder: 100.0 g.

Procedure

All the powders are passed through a screen with openings sof 0.6 mm. Then the drug substance is placed in a suitable mixer and mixed first with the talcum, then with the lactose until homogenous. No. 3 capsules are filled with 200 mg each, using a capsule filling machine.

What we claim is:

1. A process for preparing 1-(2,3-dihydro-1,4-benzodioxin-2S-yl)-5-(2,3-dihydro-1,4-benzodioxin-2R-yl)-3-azapentane-1R,5S-diol, or a salt thereof, comprising the following steps:

(a) reacting the aminoalcohol of the formula IV,

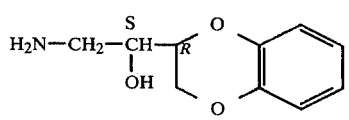 (IV)

its racemate or antipode, with an acyl halide wherein acyl represents lower alkanoyl, benzoyl or benzoyl substituted by lower alkyl, lower alkoxy or halogen;

(b) treating the resulting erythro 2-(2-acylamino-1-hydroxyethyl)-2,3-dihydro-1,4-benzodioxin with an effective dehydrating agent;

(c) reacting the resulting erythro 2-(2-aryl or lower alkyl-4,5-dihydrooxazol-5-yl)-2,3-dihydro-1,4-benzodioxin, wherein aryl represents phenyl or phenyl substituted by lower alkyl, lower alkoxy or halogen, with the oxiran of formula III, (III)

its racemate or antipode at elevated temperature;
(d) hydrolyzing the resulting compound of formula V

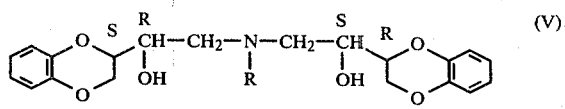

wherein R represents acyl as defined above or an isomeric mixture containing said compound; and
(e) if necessary separating the resulting mixture of isomers.

2. A process according to claim 1 wherein the term acyl represents benzoyl or benzoyl substituted by lower alkyl, lower alkoxy or halogen, and the term aryl represents phenyl or phenyl substituted by lower alkyl, lower alkoxy or halogen.

3. A process according to claim 1 for preparing the compound as defined therein comprising:
(a) reacting d,l-erythro-2-(2-amino-1-hydroxyethyl)-2,3-dihydro-1,4-benzodioxin with benzoyl chloride;
(b) treating the resulting d,l-erythro 2-(2-benzamido-1-hydroxyethyl)-2,3-dihydro-1,4-benzodioxan with thionyl chloride as a dehydrating agent;
(c) heating together the resulting d,l-erythro 2-(2-phenyl 4,5-dihydrooxazol-5-yl)-2,3-dihydro-1,4-benzodioxin, with d,l-erythro-2-oxiranyl-2,3-dihydro-1,4-benzodioxin;
(d) hydrolyzing the resulting isomeric mixture containing the compound of formula V as defined in said claim 1 wherein R represents benzoyl; and
(e) separating the resulting mixture of isomers.

* * * * *